US008648212B2

(12) United States Patent
Weiskopf et al.

(10) Patent No.: US 8,648,212 B2
(45) Date of Patent: Feb. 11, 2014

(54) PROCESS FOR PREPARING SOLUTIONS OF RADIATION-SENSITIVE, FREE-RADICALLY POLYMERIZABLE ORGANIC COMPOUNDS

(75) Inventors: Verena Weiskopf, Guntersblum (DE); Franz Niklaus Windlin, Heidelberg (DE); Harald Winsel, Freinsheim (DE); Markus Ruckpaul, Weinheim (DE); Dirk Wulff, Schifferstadt (DE); Uwe Duesterwald, Queidersbach (DE); Ulrike Licht, Mannheim (DE)

(73) Assignee: BASF SE, Ludwigshafen (DE)

( * ) Notice: Subject to any disclaimer, the term of this patent is extended or adjusted under 35 U.S.C. 154(b) by 95 days.

(21) Appl. No.: 13/258,899

(22) PCT Filed: Mar. 30, 2010

(86) PCT No.: PCT/EP2010/054202
§ 371 (c)(1),
(2), (4) Date: Sep. 22, 2011

(87) PCT Pub. No.: WO2010/112505
PCT Pub. Date: Oct. 7, 2010

(65) Prior Publication Data
US 2012/0016079 A1   Jan. 19, 2012

(30) Foreign Application Priority Data
Apr. 2, 2009   (EP) ..................... 09157168

(51) Int. Cl.
*C08F 220/10* (2006.01)
*C08K 5/07* (2006.01)
*C08F 2/06* (2006.01)

(52) U.S. Cl.
USPC ................. 560/1; 560/65; 524/770; 526/208; 526/318.4

(58) Field of Classification Search
USPC ............... 560/1, 65; 524/770; 526/208, 318.4
See application file for complete search history.

(56) References Cited

U.S. PATENT DOCUMENTS

| 2,587,437 A | | 2/1952 | Bralley et al. | |
| 5,128,386 A | * | 7/1992 | Rehmer et al. | 522/35 |
| 5,248,805 A | * | 9/1993 | Boettcher et al. | 558/270 |
| 6,964,837 B2 | * | 11/2005 | Schrof et al. | 430/139 |
| 7,091,296 B2 | * | 8/2006 | Meyer et al. | 526/319 |
| 2003/0175506 A1 | * | 9/2003 | Schrof et al. | 428/343 |
| 2005/0080213 A1 | * | 4/2005 | Meyer et al. | 526/319 |
| 2012/0016079 A1 | * | 1/2012 | Weiskopf et al. | 524/770 |

FOREIGN PATENT DOCUMENTS

| EP | 024648 | * | 5/1987 |
| EP | 0 377 191 | | 7/1990 |
| EP | 0 377 199 | | 7/1990 |
| EP | 0 655 465 | | 5/1995 |
| EP | 1 213 306 | | 6/2002 |
| JP | 2006 327986 | | 12/2006 |

OTHER PUBLICATIONS

Satsuma et al. English machine translation of JP 2006-327986. Translation obtained from AIPN/JPO website on Mar. 25, 2013.*
International Search Report Issued Jun. 25, 2010 in PCT/EP10/054202 Filed Mar. 30, 2010.

* cited by examiner

*Primary Examiner* — Liam Heincer
*Assistant Examiner* — Michael A Salvitti
(74) *Attorney, Agent, or Firm* — Oblon, Spivak, McClelland, Maier & Neustadt, L.L.P.

(57) ABSTRACT

A description is given of a process for preparing solutions of radiation-sensitive, free-radically polymerizable organic compounds, where a first starting compound, which has an acid halide group, and a second starting compound, which has an alcoholic hydroxyl group, are esterified with one another in a solvent or in a solvent mixture. The solvent comprises one or more ketones having a boiling point of below 150° C. under atmospheric pressure (1 bar), or the solvent mixture is composed to an extent of at least 50% by weight of said ketones. One of the two starting compounds has at least one radiation-sensitive group and the other of the two starting compounds has at least one ethylenically unsaturated, free-radically polymerizable group. A description is also given of corresponding solutions of radiation-sensitive, free-radically polymerizable organic compounds and of their use for preparing radiation-crosslinkable, free-radically copolymerized copolymers, more particularly for hotmelt pressure-sensitive adhesives or aqueous polymer dispersions.

6 Claims, No Drawings

PROCESS FOR PREPARING SOLUTIONS OF RADIATION-SENSITIVE, FREE-RADICALLY POLYMERIZABLE ORGANIC COMPOUNDS

CROSS REFERENCE TO RELATED APPLICATIONS

This application is a 35 U.S.C. §371 national stage patent application of international patent application PCT/EP10/054,202, filed Mar. 30, 2010, the text of which is incorporated herein by reference, and claims priority to a Europe patent application 09157168.7, filed Apr. 2, 2009, the text of which is also incorporated herein by reference.

The invention relates to a process for preparing solutions of radiation-sensitive, free-radically polymerizable organic compounds, where a first starting compound, which has an acid halide group, and a second starting compound, which has an alcoholic hydroxyl group, are esterified with one another in a solvent or in a solvent mixture of low-boiling ketones. The invention also relates to corresponding solutions of radiation-sensitive, free-radically polymerizable organic compounds and of their use for preparing radiation-curable materials, more particularly radiation-crosslinkable, free-radically copolymerized copolymers, for example, for hotmelt pressure-sensitive adhesives or aqueous polymer dispersions.

UV-crosslinkable polyacrylates and their use for hotmelt pressure-sensitive adhesives (hotmelt PSAs) are described in EP 377199 A, EP 655465 A, and EP 1213306A. The UV-crosslinkable polyacrylates comprise a photoinitiator which is incorporated into the polymer chain by free-radical copolymerization. Suitable copolymerizable photoinitiator monomers are described in EP 377191A. As the link between the photoreactive moiety and the polymerizable moiety, the photoinitiator monomers comprise an ester group, more particularly a carbonate ester group. For the preparation, a suitable acid halide is esterified with a suitable hydroxyl compound. The esterification takes place in the presence of an amine, which is used preferably in excess in order to scavenge the acid which forms, with formation of an ammonium hydrogen halide salt. Amine and ammonium salt must be separated off reliably, since they are undesirable for the subsequent copolymerization and for uses of the copolymer. For instance, even very small residual amounts of amines lead to yellowing, which adversely affects the possibility for use, in particular, as an adhesive for transparent films. The easiest way to remove the ammonium salts is by washing with water. A precondition is that there is effective phase separation between the water and the organic solvent used in the esterification reaction. Highly suitable solvents are aromatic hydrocarbons such as toluene or xylenes, for example, since they develop effective phase separation with water. Excess aromatic hydrocarbons, moreover, are easily recycled and can be used again for subsequent syntheses, since the recycled solvents are water-free and there is no risk of hydrolysis of the acid chlorides. A further advantage of relatively high-boiling hydrocarbons such as xylene, for example, is that excess low-boiling amines, such as triethylamine, for example, are easily separated off by distillation.

The aromatic hydrocarbons that are very suitable per se as solvents in the preparation of the photoinitiator monomers do, however, have the disadvantage that residual amounts remain in the subsequently prepared copolymers and in the subsequently prepared end products, such as in hotmelt PSAs, for example, and make a not inconsiderable contribution to the overall level of residual volatiles (VOC content). For numerous applications close to end users, however, a very low VOC content is desirable. Thus, for example, in applications as an adhesive tape in the interior of automobiles, for instance as tapes for the wrapping of cable harnesses (cable wrapping tapes) or as double-sided adhesive tapes for the fastening of trim parts, an excessive VOC content on the part of the adhesive may result in what is called fogging, the formation of an unwanted deposit on screens and windows. For certain applications, such as in plasters with direct skin contact, moreover, the desire is for complete absence of aromatic hydrocarbons.

In many applications of radiation-curable coating materials as well, as for example in the curing of varnish and resin coatings on paper, metal or plastic, or in the drying of printing inks and liquid inks, great importance is attached to minimizing the amount of volatile fractions. Such fractions may affect the attainable ultimate hardness of the coat or layer, or there may be unwanted changes in color, yellowing for instance. The diffusion or migration from the coating into surrounding materials may also cause problems. Particularly when the coatings or materials surrounding them come into contact with foods, very low levels, or absence, of components that are objectionable on health grounds, such as aromatic hydrocarbons, for example, is desirable.

It is therefore an object of the invention to provide an alternative process for preparing free-radically polymerizable photoinitiator monomers comprising ester groups, in which process, as far as possible, there is no need, on the one hand, for the use of aromatic hydrocarbons as solvents, and, on the other hand, it is possible to separate off amines and ammonium salts with a reliability similar to that when aromatic hydrocarbons are used, and where end products produced directly or indirectly with the photoinitiator monomers have an extremely low VOC content.

Surprisingly it has been found that this object can be achieved by using ketone solvents having a boiling point of below 150° C. under atmospheric pressure (1 bar). This is surprising in that, without knowledge of the invention, these ketones, on the basis of their physical properties, appear to be not well suited for the intended purpose. The ketones, some of which are miscible with water, frequently develop poorer phase separation with water than hydrocarbons, and so effective separation of organic phase and aqueous phase appears questionable. Some organic ammonium salts are soluble in ketones, and hence separation from the organic phase appears problematic. Ketones are at least partly water-miscible. Thus, for example, up to 12.5% by weight of water dissolves in methyl ethyl ketone. This makes it look difficult to use spent solvent again, since the water content might cause hydrolysis of the acid chlorides.

Furthermore, residues of excess amines cannot be removed from the solvent by distillation if the boiling point of the solvent (e.g., 80° C. for methyl ethyl ketone) is lower than that of the amine to be separated (e.g., 89° C. for triethylamine). However, the difficulties which make the ketones look so unsuitable have been overcome.

The invention provides a process for preparing solutions of radiation-sensitive, free-radically polymerizable organic compounds, where a) a first starting compound, which has an acid halide group, and
b) a second starting compound, which has an alcoholic hydroxyl group, are esterified with one another in a solvent or solvent mixture; and where the solvent comprises one or more ketones having a boiling point of below 150° C. under atmospheric pressure (1 bar) or the solvent mixture is composed to an extent of at least 50% by weight, based on the amount of solvent, of said ketones; and one of the two starting compounds has at least one radiation-sensitive group and the other of the two starting compounds has at least one ethylenically unsaturated, free-radically polymerizable group.

Occasionally below the expression "(meth)acrylate" and similar expressions will be used as an abbreviated notation for "acrylate or methacrylate".

Radiation-sensitive, free-radically polymerizable organic compounds are referred to below for short as polymerizable photoinitiator. The polymerizable photoinitiator can be incorporated into the polymer chain of copolymers by means of free-radical copolymerization. Polymerizable photoinitiators preferably have the following basic structure:

A-X-B where A is a monovalent organic radical which as its radiation-sensitive group preferably has a phenone group, X is an ester group, selected from —O—C(=O)—, —(C=O)—O—, and —O—(C=O)—O—, and B is a monovalent organic radical which comprises an ethylenically unsaturated free-radically polymerizable group. Preferred radicals A are radicals comprising at least one structural element derived from phenones, more particularly from acetophenones or benzophenones. Preferred radicals B comprise at least one, preferably just one acrylic or methacrylic group.

The ethylenically unsaturated group may be attached directly to the group X. It is also possible for the radiation-sensitive group to be attached directly to the group X. Alternatively, between ethylenically unsaturated group and group X, or between radiation-sensitive group and group X, there may in each case be a spacer group positioned. The spacer group may have, for example, a molecular weight of up to 500, more particularly up to 300 or 200 g/mol.

Examples of suitable photoinitiators include compounds with acetophenone or benzophenone structural units, described in EP 377191A or EP 1213306 A, for example. A preferred group X is the carbonate group —O—(C=O)—O—. Preferred polymerizable photoinitiators are compounds of the formula:

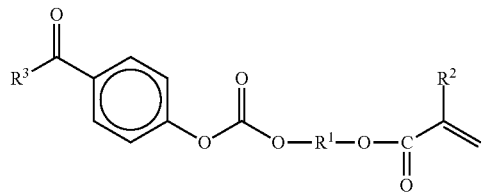

in which R1 is an organic radical having up to 30 C atoms, R2 is an H atom or a methyl group, and R3 is a substituted or unsubstituted phenyl group or is a C1-C4 alkyl group. R1 is more preferably an alkylene group, more particularly a C2-C8 alkylene group. R3 is more preferably a methyl group or a phenyl group, very preferably a phenyl group.

Further acetophenone derivatives and benzophenone derivatives that are suitable as copolymerizable photoinitiators are, for example, those of the formula

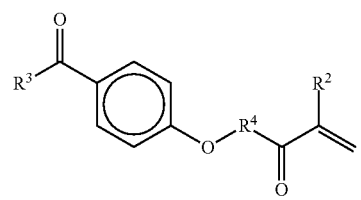

in which R2 and R3 can have the definition above and R4 can be a single bond or (—CH2-CH2-O)n, where n is an integer from 1 to 12.

The first starting compound for preparing the polymerizable photoinitiator has an acid halide group. An acid chloride group is preferred, more preferably a chloroformate group Cl—C(=O)—O—. The second starting compound has an alcoholic hydroxyl group. This may be an aliphatic or aromatic, more particularly phenolic, hydroxyl group. The copolymerizable photoinitiators are preferably carbonates. They are preparable by reacting carbonic ester chlorides with alcohols. In one preferred embodiment the first starting compound has a chloroformate group and an acrylate or methacrylate group, and the second starting compound has an alcoholic hydroxyl group and a phenone group. The starting compounds can be prepared by known processes: a compilation is found, for example, in EP 377 191A.

In accordance with the invention, the polymerizable photoinitiator is prepared by esterification in a solvent or solvent mixture. The solvent or solvent mixture comprises one or more ketones having a boiling point of below 150° C., preferably below 130° C., under standard pressure (1 bar), or the solvent mixture is composed to an extent of at least 50% by weight, based on the amount of solvent, of said ketones. The boiling range of the solvents is preferably from 50 to below 150° C., more particularly from 60 to 120° C. Preference is given to dialkyl ketones having a boiling point in the range from 50 to below 130° C. The amount of polymerizable photoinitiator in the solutions prepared in accordance with the invention is preferably from 5% to 85%, preferably 20% to 60% by weight. Suitable ketones generally have a molar weight of below 150 g/mol. Examples include acetone, methyl ethyl ketone (MEK, 2-butanone) or methyl isobutyl ketone (MIBK). MEK and MIBK are particularly preferred. The ketones or mixtures of these ketones are more preferably the sole solvent. Alternatively they may be present in a mixture with other solvents. In the case of a solvent mixture of this kind, the fraction of the ketones is at least 50% by weight, based on the total amount of solvent, and is preferably at least 80% by weight, more preferably at least 95% by weight. With very particular preference the solvent is solely and exclusively methyl ethyl ketone or methyl isobutyl ketone.

Surprisingly it has been found that, in spite of the sensitivity of the acid halide to hydrolysis, it is not absolutely necessary to operate in complete absence of moisture. This allows the use more particularly of solvents or solvent mixtures which are not completely water-free. As a result of this it is possible for at least some of the ketone solvents used to be recycled hydrous ketones recovered from a prior preparation process by means, for example, of azeotropic distillation. Thus, for example, methyl ethyl ketone may comprise water up to the saturation limit (approximately 12.5% by weight), e.g., at least 1% or at least 5% by weight of water.

The starting compounds are used preferably in an equimolar ratio, though optionally an excess of up to 10 to 30 mol % of one of the starting compounds can also be used. The starting compounds are esterified preferably in the presence of a basic, nonnucleophilic amine. Generally speaking, a solution or suspension of the hydroxy compound in the solvent is introduced in the presence of a basic, nonnucleophilic amine, and the acid halide is added. Examples of amines include triethylamine, 4-dimethylaminopyridine, imidazole, 1,4-diazabicyclo[2.2.2]octane, 1,5-diazabicyclo[4.3.0]non-5-ene, 1,8-diazabicyclo[5.4.0]undec-7-ene, polyvinylpyridine, N,N'-dimethylpropyleneurea or N,N'-dimethylethyleneurea. Particular preference is given to tertiary organic amines, more particularly those of the formula $NR_3$, where R is an alkyl group having 1 to 10, preferably 2 to 4, C atoms.

The amount of amine used is preferably substantially stoichiometric, i.e., the amount of amine is equimolar to the amount of acid halide, though it is also possible, optionally, to use an excess of up to 5 mol % or up to 10 mol % of amine. The acid halide compound (optionally in solution in the solvent of the reaction medium) is added dropwise with stirring. The esterification reaction takes place preferably at temperatures of 0 to 100° C., preferably at 10 to 50° C. After a subsequent stirring time of 1 to 48 hours, preferably 1 to 20 hours, at 10 to 50° C., for example, the ammonium salts formed and any excess amine, following addition of water or dilute hydrochloric acid, are separated off by means of phase separation. Excess amine can also be removed by distillation.

In order to prevent premature polymerization of the free-radically polymerizable reactants and products, it is preferred to add a customary stabilizer to the reaction mixture. Examples of suitable such stabilizers include hydroquinone, hydroquinone monomethyl ether, 2,6-di-tert-butyl-4-methylphenol, para-nitrosophenol, 2,2,6,6-tetramethylpiperidinyloxyl (TEMPO) and/or phenothiazine. Furthermore, it has proven extremely advantageous to pass oxygen or air with an oxygen content of 1-20% through the reaction mixture in the course of acylation.

Surprisingly it has emerged that, in spite of the poor phase separation of pure ketone solvent and water, the partial mutual miscibility of ketone and water, and the partial solubility of organic ammonium compounds in ketones, the organic ammonium compounds that form in the esterification reaction can be separated sufficiently well from the solution of the photoinitiator in ketone. It has been found particularly advantageous to carry out the separation of the organic ammonium halide which forms during the reaction after the reaction by adding water in an amount such as to form a substantially saturated solution of the organic ammonium halide in water, and this saturated aqueous solution is separated from the organic phase. The amount of water is calculated such that on the one hand it does not exceed the amount required to form a saturated solution, or does not substantially exceed the amount required theoretically, i.e., by not more than 10% by weight, preferably by not more than 5% by weight. And, then again, the amount of water should as far as possible be enough that all or virtually all of the ammonium halides, i.e., to an extent of at least 90% by weight, preferably to an extent of at least 95% by weight, are in solution. The saturated aqueous ammonium salt solution in this case forms effective phase separation with the organic phase and is easy to separate off.

Small fractions of ammonium halides that have remained in solution in the organic phase can be separated off by means of low-temperature precipitation. For this purpose the temperature of the organic phase is lowered below room temperature to an extent such that the ammonium halides crystallize out of the organic phase. Cooling takes place preferably to 0° C. or below, more preferably to −5° C. or below or to −10° C. or below. The precipitated salts can be isolated by filtration.

Amines are used preferably only in stoichiometric amounts. If, nevertheless, excess residual amounts of amines are present after the reaction, they can be converted into ammonium salts by neutralization with an acid, and separated off as above, and/or the residual amines can be removed by distillation, in the form of an azeotrope, for example. Through the combination in particular of the various measures, such as (i) very substantial avoidance of excess amines through use of stoichiometric amounts, (ii) conversion into ammonium salts and their separation, and (iii) distillative purification, it is possible to remove the amines to a point where the yellowing in end products that is caused by traces of amine, the end products having been produced using the copolymerizable photoinitiator, can be avoided.

The invention also provides for the use of the above-described solutions of copolymerizable photoinitiators for preparing radiation-curable materials, more particularly those based on radiation-crosslinkable, free-radically copolymerizable copolymers. Inventive uses are, for example, the preparation of radiation-curable hotmelt PSAs, radiation-curable aqueous polymer dispersions, radiation-curable coating materials, radiation-curable paints, radiation-curable printing inks, radiation-curable liquid inks, radiation-curable screen-printing materials, and radiation-curable surface coatings on food packaging.

Particular preference is given to the use for the preparation of hotmelt PSAs or of aqueous polymer dispersions, as for example for the preparation of UV-curable adhesives or for the preparation of UV-curable coating materials. The copolymers are preferably polyacrylate copolymers. A polyacrylate copolymer is a polymer obtainable through free-radical addition polymerization of acrylic monomers, a term also taken to include methacrylic monomers, and of further, copolymerizable monomers. With preference the polyacrylate copolymer is composed to an extent of at least 40%, more preferably at least 60%, very preferably at least 80%, by weight of C1-C10 alkyl (meth)acrylates. Mention may be made more particularly of C1-C8 alkyl (meth)acrylates, e.g., methyl (meth)acrylate, ethyl (meth)acrylate, n-butyl (meth)acrylate, and 2-ethylhexyl (meth)acrylate. The polyacrylate copolymer is crosslinkable with UV light. The photoinitiator is attached to the polyacrylate. Through irradiation with high-energy light, more particularly UV light, the photoinitiator brings about crosslinking of the polymer, preferably by means of a chemical grafting reaction of the photoinitiator with a spatially adjacent polymer chain. More particularly the crosslinking may take place through insertion of a carbonyl group of the photoinitiator into an adjacent C—H bond, with formation of a —C—C—O—H moiety. The polyacrylate copolymer contains preferably 0.0001 to 1 mol, more preferably 0.0002 to 0.1 mol, very preferably 0.0003 to 0.01 mol, of the photoinitiator, or of the molecular group attached to the polymer and effective as a photoinitiator, per 100 g of polyacrylate copolymer. Further, nonacrylate monomers of which the polyacrylate copolymer may additionally be composed include, for example, vinyl esters of carboxylic acids comprising up to 20 C atoms, vinylaromatics having up to 20 C atoms, ethylenically unsaturated nitriles, vinyl halides, vinyl ethers of alcohols comprising 1 to 10 C atoms, aliphatic hydrocarbons having 2 to 8 C atoms and 1 or 2 double bonds, or mixtures of these monomers. Examples of suitable vinylaromatic compounds include vinyltoluene, α- and p-methylstyrene, alpha-butylstyrene, 4-n-butylstyrene, 4-n-decylstyrene, and, preferably, styrene. Examples of nitriles are acrylonitrile and methacrylonitrile. The vinyl halides are chlorine-, fluorine- or bromine-substituted, ethylenically unsaturated compounds, preferably vinyl chloride and vinylidene chloride. Vinyl ethers include, for example, vinyl methyl ether or vinyl isobutyl ether. Preference is given to vinyl ethers of alcohols comprising 1 to 4 C atoms. Hydrocarbons having 2 to 8 C atoms and two olefinic double bonds include butadiene, isoprene, and chloroprene. Further suitable monomers also include, in particular, monomers having carboxylic, sulfonic or phosphonic acid groups. Carboxylic acid groups are preferred. Examples include acrylic acid, methacrylic acid, itaconic acid, maleic acid or fumaric acid. Further monomers are, for example, also (meth)acrylamide and monomers comprising hydroxyl groups, especially C1-C10 hydroxyalkyl (meth)acrylates. Mention may additionally be made of phenyloxyethyl glycol mono(meth)acrylate, glycidyl acrylate, glycidyl methacrylate, and amino (meth)acrylates such as 2-aminoethyl(meth)acrylate. Monomers which as well as the double bond also carry other functional groups, examples being isocyanate-, amino-, hydroxy-, amid- or glycidyl-, may have the effect, for example, of improving the adhesion to substrates.

The polyacrylate copolymer preferably has a K value of 30 to 80, more preferably of 40 to 60, as measured in tetrahydrofuran (1% strength solution, 21° C.). The K value of Fikentscher is a measure of the molecular weight and the viscosity of the polymer. The glass transition temperature (Tg) of the polyacrylate copolymer is preferably −60 to +10° C., more preferably −55 to 0° C., very preferably −55 to −10° C. The glass transition temperature can be determined by customary methods such as differential thermal analysis or differential scanning calorimetrie (see, for example, ASTM 3418/82, midpoint temperature).

The polyacrylate copolymers can be prepared by copolymerizing the monomeric components using the customary polymerization initiators and also, where desired, regulators, with polymerization taking place at the customary temperatures in bulk, in emulsion, e.g., in water or liquid hydrocarbons, or in solution. Preferably the polyacrylate copolymers are prepared either by emulsion polymerization in water or by polymerization of the monomers in organic solvents, more particularly in organic solvents with a boiling range of 50 to 150° C., preferably of 60 to 120° C., using the customary amount of polymerization initiators, which is generally 0.01% to 10%, more particularly 0.1% to 4%, by weight, based on the total weight of the monomers.

The copolymers can be prepared at temperatures of 20 to 150° C., preferably at temperatures in the range from 70 to 120° C., under pressures of 0.1 to 100 bar (absolute), preferably at 0.3 to 10 bar, in the presence of 0.01% to 10% by weight of peroxides or azo initiators as polymerization initiators, based on the monomers, and in the presence of 0% to 200% by weight of inert solvents, preferably 5% to 25% by weight, based on the monomers, i.e., prepared by solution polymerization or bulk polymerization. Preferably the reaction takes place with a progression in reduced pressure, accomplished, for example, by lowering the pressure from atmospheric pressure (1 bar) to 500 mbar (absolute). Examples of solvents are hydrocarbons, alcohols such as methanol, ethanol, propanol, butanol, and isobutanol, ketones such as acetone, methyl ethyl ketone and methyl isobutyl ketone, ethyl acetate, nitriles such as acetonitrile and benzonitrile, or mixtures of the solvents stated.

In one preferred embodiment the solvent used for the polymerization is the same solvent as that for the inventive preparation of the copolymerizable photoinitiator, i.e., one or more ketones having a boiling point of below 150° C. under atmospheric pressure (1 bar).

Examples of suitable polymerization initiators include azo compounds, ketone peroxides, and alkyl peroxides, e.g., acyl peroxides such as benzoyl peroxide, dilauroyl peroxide, didecanoyl peroxide, isononanoyl peroxide, alkyl esters such as tert-butyl tert-pivalate, tert-butyl per-2-ethylhexanoate, tert-butyl permaleate, tert-butyl per-isononanoate, tert-butyl perbenzoate, tert-amyl per-2-ethylhexanoate, dialkyl peroxides such as dicumyl peroxide, tert-butyl cumyl peroxide, di-tert-butyl peroxide, and peroxodicarbonates. As initiators it is additionally possible to use azo initiators such as, for example, 2,2'-azobisisobutyronitrile, 2,2'-azobis(methyl isobutyrate) or 2,2'-azobis(2,4-dimethylvaleronitrile).

For the conduct of the polymerization it is also possible to add polymerization regulators, compounds which lower the degree of polymerization, to the reaction mixture, in amounts, for example, of 0.1 to 0.8 part by weight, based on 100 parts by weight of the monomers to be polymerized. Suitability is possessed, for example, by compounds having a thiol group, examples being mercaptans such as mercaptoethanol, tert-butyl mercaptan, mercaptosuccinic acid, ethyl hexyl thioglycolate, 3-mercaptopropyltrimethoxysilane or dodecyl mercaptan. In one embodiment no molecular weight regulators are used.

The invention also provides a process for preparing aqueous polymer dispersions, where
(i) an above-described solution of a copolymerizable photoinitiator is provided and
(ii) the radiation-sensitive, free-radically polymerizable organic compound present in the solution is subjected to free-radical copolymerization with different free-radically polymerizable monomers, to form radiation-crosslinkable copolymers, by emulsion polymerization or suspension polymerization in the presence of an aqueous phase.

The polymers are prepared preferably in the form of an emulsion polymer by emulsion polymerization. The emulsion polymerization takes place with the use of emulsifiers and/or protective colloids, or stabilizers, as surface-active substances. As surface-active substances it is preferred to use exclusively emulsifiers, whose molecular weights, unlike those of the protective colloids, are usually below 2000 g/mol. As surface-active substances it is preferred to use anionic and nonionic emulsifiers. Commonplace emulsifiers are, for example, ethoxylated fatty alcohols (EO degree: 3 to 50, alkyl radical: $C_8$ to $C_{36}$), ethoxylated mono-, di-, and trialkylphenols (EO degree: 3 to 50, alkyl radical: $C_4$ to $C_9$), and alkali metal salts and ammonium salts of alkyl sulfates (alkyl radical: $C_8$ to $C_{12}$), of ethoxylated alkanols (EO degree: 4 to 30, alkyl radical: $C_{12}$ to $C_{18}$), of ethoxylated alkylphenols (EO degree: 3 to 50, alkyl radical: $C_4$ to $C_9$), of alkylsulfonic acids (alkyl radical: $C_{12}$ to $C_{18}$), and of alkylarylsulfonic acids (alkyl radical: $C_9$ to $C_{18}$). Commercial products of suitable emulsifiers are, for example, Dowfax®2 A1, Emulan® NP 50, Dextrol® OC 50, Emulgator 825, Emulgator 825 S, Emulan® OG, Texapon® NSO, Nekanil® 904 S, Disponil® FES 77, Lutensol® AT 18, Steinapol VSL, and Emulphor NPS 25.

The emulsion polymerization can be started using water-soluble initiators. One preferred embodiment of the invention uses one or more initiators, the total amount of initiator being less than 0.4 pphm (parts per hundred monomer; parts per weight per hundred parts by weight of monomer), more particularly not more than 0.3 pphm, e.g., from 0.1 or from 0.2 to 0.3 pphm. Water-soluble initiators are exemplified by ammonium and alkali metal salts of peroxodisulfuric acid, e.g., sodium peroxodisulfate, hydrogen peroxide or organic peroxides, e.g., tert-butyl hydroperoxide. Also suitable as initiators are what are known as reduction-oxidation (redox) initiator systems. The redox initiator systems are composed of at least one, usually inorganic, reducing agent and an organic or inorganic oxidizing agent. The oxidation component comprises, for example, the aforementioned initiators for the emulsion polymerization. The reduction component comprises, for example, alkali metal salts of sulfurous acid, such as sodium sulfite, sodium hydrogensulfite, alkali metal salts of disulfurous acid such as sodium disulfite, bisulfite addition compounds with aliphatic aldehydes and ketones, such as acetone bisulfite, or reducing agents such as hydroxymethanesulfinic acid and salts thereof, or ascorbic acid. The redox initiator systems can be used with the accompaniment of soluble metal compounds whose metallic component is able to exist in a plurality of valence states. Examples of customary redox initiator systems are ascorbic acid/iron(II)sulfate/sodium peroxydisulfate, tert-butyl hydroperoxide/sodium disulfite, tert-butylhydroperoxide/Na hydroxymethanesulfinate. The individual components, the reducing component for example, may also be mixtures: for example, a mixture of the sodium salt of hydroxymethanesulfinic acid with sodium disulfite. Also possible is the use of two or more different initiators in the emulsion polymerization.

The polymerization medium may be composed either of water alone or of mixtures of water and water-miscible liquids such as methanol. It is preferred to use just water. The emulsion polymerization can be carried out either as a batch operation or in the form of a feed process, including staged or gradient procedures. Preference is given to the feed process, where a portion of the polymerization batch is introduced as the initial charge, heated to the polymerization temperature, and partially polymerized, and then the remainder of the polymerization batch is fed to the polymerization zone continuously, in stages or under a concentration gradient, while the polymerization is maintained. In the polymerization it is also possible to include a polymer seed in the initial charge for the purpose, for example, of setting the particle size more effectively.

The emulsion polymerization produces aqueous dispersions of the polymer in general with solids contents of 15% to 75%, preferably of 20% to 70% or of 40% to 70% by weight. In one embodiment the dispersion or pressure-sensitive adhesive comprises at least 60% by weight of dispersed polymer. In order to be able to achieve solids contents >60% by weight, a bimodal or polymodal particle size ought to be set, since otherwise the viscosity becomes too high and the dispersion is no longer manageable. Producing a new generation of particles can be accomplished, for example, by addition of seed before or during the emulsion polymerization, by addition of excess amounts of emulsifier or by addition of miniemulsions. A further advantage associated with the low viscosity and high solids content is the improved coating behavior at high solids contents. One or more new generations of particles can be produced at any desired point in time. A particular point in time is guided by the target particle size distribution for a low viscosity.

The copolymers prepared by emulsion polymerization in accordance with the invention are used preferably in the form of an aqueous dispersion. The average size of the polymer particles dispersed in the aqueous dispersion is preferably from 100 to 500 nm. The size distribution of the particles in the dispersion may be monomodal, bimodal or multimodal. In the case of a monomodal particle size distribution, the average size of the polymer particles dispersed in the aqueous dispersion is preferably less than 500 nm. In the case of bimodal or multimodal particle size distribution, the particle size may also be up to 1000 nm. By average particle size here is meant the $d_{50}$ figure of the particle size distribution, i.e., 50% by weight of the total mass of all the particles have a particle diameter smaller than the $d_{50}$ figure. The particle size distribution may be determined in a known way using the analytical ultracentrifuge (W. Mächtle, Makromolekulare Chemie 185 (1984), pages 1025-1039).

One advantage of the polymer dispersions prepared by emulsion polymerization in accordance with the invention is that it is possible in a simple way to provide UV-crosslinkable dispersions which are free from residual volatile aromatic hydrocarbons, and which overall have a very low fraction of volatile organic compounds (VOC). Residues of the ketone solvent used in the preparation of the photoinitiator monomer can be removed from the aqueous dispersion in a simple way by means of azeotropic distillation.

The invention also provides a process for preparing hotmelt pressure-sensitive adhesives, where
(i) an above-described solution of a copolymerizable photoinitiator is provided and
(ii) the radiation-sensitive, free-radically polymerizable organic compound present in the solution is subjected to free-radical copolymerization with different free-radically polymerizable monomers, to form radiation-crosslinkable copolymers, preferably radiation-crosslinkable polyacrylates, in an organic solvent, and
(iii) the organic solvent is removed.

There is a need to lower the residual volatiles, especially unreacted monomers and solvent residues, to a minimum. For the separation of solvents (evaporative removal of the solvent, with retention of the polyacrylate melt) there are a very wide variety of technical methods available, examples being kettle distillation, the use of a falling-film evaporator, strand devolatilization or residual devolatilization in an extruder. In principle there are a host of methods for separating residual volatiles from polymer melts. Economic devolatilization of relatively high-viscosity polymer melts is accomplished, for example, by strand devolatilization or by treatment of the products in a devolatilizing extruder. One preferred method is that described in EP 655465 A of eliminating residual volatiles from polyacrylate melts. In this method the volatile fractions are evaporated off under reduced pressure and toward the end of the distillation, under reduced-pressure conditions, an entraining agent such as steam, nitrogen, argon or $CO_2$ is forced into the hot polyacrylate melt (at temperatures of above 100° C., for example), the melts being pumped in circulation at the same time. Subsequently the entraining agent is stripped off together with the residual volatiles. A particularly advantageous entraining agent is steam.

The hotmelt PSA of the invention is suitable for producing hotmelt PSA coatings, on labels, adhesive tapes, and films, for example. The labels may be made, for example, of paper or plastics such as polyesters, polyolefins or PVC. The adhesive tapes or films may likewise be made of the above plastics. To produce the coatings, the hotmelt PSAs can be applied, preferably in melt form, to the target substrates, i.e., the solvent is removed beforehand by suitable methods, preferably down to a residual level of less than 0.5% by weight, based on the polyacrylate copolymer. Thereafter the composition can be applied as a melt, i.e., generally at temperatures of 80 to 160° C., to substrates of the kind exemplified above. Preferred coat thicknesses are, for example, 1 to 200 micrometers, more preferably 2 to 80, very preferably 5 to 80 micrometers. The polyacrylate copolymers that are crosslinkable with UV light can then be irradiated with high-energy radiation, preferably UV light, and so crosslinking takes place. Generally speaking, for this purpose, the coated substrates are placed on a conveyor belt and the belt is conveyed past a radiation source, a UV lamp for example. The degree of crosslinking of the polymers is dependent on the duration and intensity of the irradiation. The radiant energy preferably amounts in total to 100 to 1500 $mJ/cm^2$ of irradiated surface area. The coated substrates obtained may find use preferably as self-adhesive articles, such as labels, adhesive tapes or protective films. The resultant, UV-crosslinked hotmelt PSA coatings have good performance properties, such as good adhesion and high internal strength, for example, and are notable for particularly low fractions of volatile organic compounds (VOC), and more particularly for absence of aromatic hydrocarbons.

The copolymers prepared in accordance with the invention can be used, furthermore, as UV-crosslinkable compositions for the production of coatings, coverings, and impregnated systems, more particularly for producing pressure-sensitive adhesives, pressure-sensitive adhesive films, pressure-sensitive adhesive tapes, pressure-sensitive adhesive labels, and embossing foils. These compositions can be applied in a conventional way, by spreading, spraying, rolling, knife coating or pouring, if desired at elevated temperature, usually in the temperature range from 20 to 180° C., to typical substrates, such as to paper, cardboard, wood, glass, metals, metallic foils and polymeric films, such as to plasticized PVC, polypropylene, polyethylene, polyamides, polyesters, or aluminum and copper, for example. It is also possible, moreover, to coat nonwovens, fibers, leathers, and woven textile fabrics. The copolymers can also be applied to substrates such as paper for the purpose, for example, of producing pressure-sensitive adhesive labels in transfer application, by first applying them to carrier materials with a nonstick coating, such as siliconized paper, and, in the case of the UV-crosslinkable compositions, subjecting them to irradiation and subsequently, for example, to lamination to paper. After the siliconized paper has been removed, the adhesive layer can if desired be irradiated again. UV sources which can be used are the customary sources, examples being medium-pressure mercury lamps with a radiant output of 80 to 240 watts/cm. The pressure-sensitive adhesive products can be converted and/or modified in conventional form.

In one embodiment the copolymers prepared in accordance with the invention are used for producing adhesive compositions. The solvent or dispersion medium of the adhesive composition may be composed either of water alone or else of mixtures of water and water-miscible liquids such as methanol or ethanol. It is preferred to use just water. The pH of the polymer dispersion or of the adhesive composition is set preferably at a pH of more than 4.5, more particularly at a pH of between 5 and 9.5. The adhesive compositions may be composed solely of the solvent and the polymer. The adhesive composition may, however, also comprise further additives as well, examples being fillers, dyes, flow control agents, thickeners (preferably associative thickeners), defoamers, pigments, wetting agents or tackifiers (tackifying resins). For improved surface wetting the adhesives may comprise wetting assistants, examples being fatty alcohol ethoxylates, alkylphenol ethoxylates, nonylphenol ethoxylates, polyoxyethylenes, polyoxypropylenes or sodium dodecylsulfonates. The amount of additives is generally 0.05 to 5 parts by weight, more particularly 0.1 to 3 parts by weight, per 100 parts by weight of polymer (solids).

The adhesive composition of the invention is preferably a pressure-sensitive adhesive (PSA), i.e., it has pressure-sensitive adhesive properties particularly after UV crosslinking. A PSA is a viscoelastic adhesive whose set film at room temperature (20° C.) in the dry state remains permanently tacky and adhesive. Bonding to substrates is accomplished immediately upon gentle applied pressure. The adhesive composition of the invention can be used for producing self-adhesive articles. The articles are at least partly coated with the PSA. In one embodiment the self-adhesive articles can be removed again after bonding. These self-adhesive articles may be, for example, sheets, tapes or labels. Self-adhesive tapes of the invention are appropriate for a large number of fields of use, for instance as single-sided and double-sided adhesive tapes, as carrierless systems or as plasters or patches. Examples of suitable carrier materials include paper, polymeric films, metal foils or textile carriers. Self-adhesive tapes of the invention may be tapes of the above substances that are coated on one or both sides. Self-adhesive labels of the invention may be labels made of paper or a thermoplastic film. Suitable thermoplastic films include, for example, films of polyolefins (e.g., polyethylene, polypropylene), polyolefin copolymers, films of polyesters (e.g., polyethylene terephthalate) or polyacetate. The surfaces of the thermoplastic polymer films are preferably corona-treated. The labels are coated with adhesive on one side. Preferred substrates for the self-adhesive articles are paper and polymer films. Preferred self-adhesive articles are adhesive tapes. The articles are coated at least partly on at least one surface with an adhesive composition of the invention. The adhesive may be applied to the articles by customary methods such as knife coating or spreading. The application rate is preferably 1 to 120 g, more preferably 30 to 80 g, of solids per $m^2$. Application is generally followed by a drying step to remove the water and/or the solvents, and also by crosslinking through irradiation with UV light. The substrates to which the self-adhesive articles may advantageously be applied may be, for example, metal, wood, glass, paper or plastic. The self-adhesive articles are suitable for application especially to packaging surfaces, cartons, plastic packaging, books, windows, motor vehicle bodies, bodywork parts or cables.

The adhesive composition of the invention can be used with advantage in the cable harness industry for the production of self-adhesive tapes. Depending on the requirement and the field of use, articles with woven fabric, nonwoven or films of a variety of materials are used. This kind of adhesive tapes can be installed in all regions of automobiles, such as in the engine compartment or in the interior, for example. In cable bandaging, these adhesives also provide protection from unwanted interactions with the PVC core insulation. Carriers for cable-wrapping tapes used are preferably woven fabrics, nonwovens, films, paper, felts, foams or coextrudates.

The adhesive composition of the invention may also be used with advantage for producing self-adhesive tapes for medical products such as plasters, patches, and bandages for example. Carrier materials suitable for medical products are exemplified by films, of polypropylene, polyethylene or polyester, for example, woven fabrics, of cotton, viscose, viscose acetate or viscose staple, for example, but also nonwovens, of viscose or polyester, for example, and also other blends.

For the production of textile adhesive tapes, the adhesive composition of the invention may be applied to textile carrier materials, examples being woven viscose staple fabric, viscose staple fabric with an acrylate coating, woven polyester fabric, stitchbonded polyester nonwovens, waterjet-consolidated polyester nonwovens, spunbonded nonwoven with single-sided calendering, nonwovens with a coating of release agent, needlefelts with a reverse-side surface consolidated by partial melting, or thermally consolidated nonwovens. Carriers suitable for producing adhesive tapes which can be wound onto themselves are tapelike carriers composed, for example, of a thermally consolidated nonwoven, and provided on one side with an adhesive composition of the invention, it being possible for the nonwoven to have a basis weight of 10-50 $g/m^2$, a tape thickness of 0.15-0.40 mm, a tensile strength of 10-35 N/cm, and an elongation at break of 40%-75%, and the adhesive coating being composed of an acrylate adhesive of the invention which is crosslinkable by ultraviolet radiation. Also possible, however, is the use of nonwovens having a higher basis weight, an example being an adhesive tape for the bandaging of cable harnesses that comprises a thermally consolidated spunbonded nonwoven carrier composed of polypropylene, for example, with a nonwoven weight of 60 to 100 g/m$^2$, a nonwoven thickness of 400 to 600 micrometers, for example, a linear filament density of 2 dtex to 7 dtex, for example, a tensile strength of 200 N/(5 cm) to 270 N/(5 cm), for example, and an elongation at break of 55% to 85%, for example. The nonwovens used as carriers may be composed, for example, of polypropylene or polyester fibers. The coated side is preferably the smoother side, giving the tape the sound-damping quality that is desired in the context of its use as a cable-wrapping tape in the automobile industry. On the basis of the low VOC content, and absence of fogging, the copolymers can be employed with advantage as coatings or adhesives in areas with a sensitivity toward VOC's, as for example in medicine as patches and plasters, in the interior of automobiles, as cable-wrapping tapes or as double-sided adhesive tapes, for example.

The inventive solutions of radiation-sensitive compounds can also be employed with advantage in the UV curing of coating materials, such as of thin layers of radiation-curable surface coatings, for example. Coating may take place on all of the substrates that are customary for these purposes, as for example on paper, wood, textile substrates, plastic or metal. A further field of use is in the drying and/or curing of printing inks and screen-printing materials, particularly in the surface coating or surface design of cans, tubes, and metal closure caps. In view of the sharply reduced level of volatile fractions and the absence of aromatic hydrocarbons after curing has taken place, particular advantage is attached to those applications in which diffusion or migration of substances into substrate materials adjacent to the coating is to be minimized or ruled out, as in the case, for example, of coated packaging materials which come into contact with comestibles.

One field of use in accordance with the invention is the production of radiation-curable coating compositions. Radiation-curable compositions have found widespread application in the art, especially as high-grade coating materials for surfaces. Radiation-curable compositions are preparations which comprise ethylenically unsaturated polymers or prepolymers and which, where appropriate after a physical drying step, are cured by exposure to high-energy radiation, e.g., by irradiation with UV light.

Suitable curable constituents of radiation-curable coating compositions are, for example, ethylenically unsaturated urethanes (A), monoethylenically unsaturated reactive diluents (B) or, generally, polyfunctional polymerizable compounds (C) having more than one, preferably at least two, free-radically polymerizable group(s). These substances can be used alone or in combination. Suitable constituents (A), (B), and (C) and combinations thereof are described in WO 2008/155352, for example. Examples of ethylenically unsaturated urethanes (A) are aliphatic or cycloaliphatic urethane (meth) acrylates having two or more ethylenically unsaturated double bonds per molecule, their polymers, oligomers or prepolymers. Examples of suitable monoethylenically unsaturated reactive diluents (B) are compounds which comprise at least one cycloaliphatic or at least one heterocyclic group, examples being esters of acrylic acid or of methacrylic acid with cycloalkanols or bicycloalkanols, the cycloalkanol or bicycloalkanol having from 3 to 20 C atoms, preferably 5 to 10 C atoms, and being optionally substituted by $C_1$ to $C_4$ alkyl. Examples of cycloalkanol and bicycloalkanol are cyclopentanol, cyclohexanol, cyclooctanol, cyclododecanol, 4-methylcyclohexanol, 4-isopropylcyclohexanol, 4-tert-butylcyclohexanol (preferably in cis configuration), dihydrodicyclopentadienyl alcohol, isoborneol, and norbornyl alcohol. Preference is given to isoborneol, cyclohexanol, and 4-tert-butylcyclohexanol. Reactive diluents with a heterocyclic group are, for example, monofunctional esters of α,β-ethylenically unsaturated carboxylic acids (preferably acrylic acid or methacrylic acid) with monofunctional alkanols which have at least one saturated 5-membered or 6-membered heterocycle having one or two oxygen atoms in the ring as a structural element. The 5- or 6-membered, saturated heterocycle derives preferably from tetrahydrofuran, tetrahydropyran, 1,3-dioxolane, 1,3- or 1,4-dioxane. Particular preference is given to trimethylolpropane monoformal acrylate, glycerol monoformal acrylate, 4-tetrahydropyranyl acrylate, isobornyl acrylate, 2-tetrahydropyranyl methylacrylate, tetrahydrofurfuryl acrylate, and mixtures thereof. Suitable polyfunctional compounds (C) are, for example, polyfunctional (meth)acrylates which carry more than 1, preferably 2 to 10, more preferably 2 to 6 or 2 to 4 or 2 to 3 (meth)acrylate groups, preferably acrylate groups, examples being esters of (meth)acrylic acid with correspondingly at least dihydric polyalcohols. Polyalcohols are, for example, at least dihydric polyols, polyetherols or polyesterols or polyacrylate polyols having an average OH functionality of at least 2, preferably 3 to 10. Examples of polyfunctional polymerizable compounds (C) are ethylene glycol diacrylate, 1,2-propanediol diacrylate, 1,3-propanediol diacrylate, 1,4-butanediol diacrylate, 1,3-butanediol diacrylate, 1,5-pentanediol diacrylate, 1,6-hexanediol diacrylate, 1,8-octanediol diacrylate, neopentylglydol diacrylate, 1,1-, 1,2-, 1,3-, and 1,4-cyclohexanedimethanol diacrylate, 1,2-, 1,3- or 1,4-cyclohexanediol diacrylate, trimethylolpropane triacrylate, ditrimethylolpropane pentaacrylate or hexaacrylate, pentaerythrityl triacrylate or tetraacrylate, glycerol diacrylate or triacrylate, and also diacrylates and polyacrylates of sugar alcohols, such as, for example, sorbitol, mannitol, diglycerol, threitol, erythritol, adonitol (ribitol), arabitol (lyxitol), xylitol, dulcitol (galactitol), maltitol or isomalt, or of polyesterpolyols, polyetherols, poly-1,3-propanediol having a molar mass between 134 and 1178, polyethylene glycol having a molar mass between 106 and 898, and also epoxy (meth)acrylates, urethane (meth)acrylates or polycarbonate (meth)acrylates. Preferred polyfunctional polymerizable compounds (C) are ethylene glycol diacrylate, 1,2-propanediol diacrylate, 1,3-propanediol diacrylate, 1,4-butanediol diacrylate, 1,6-hexanediol diacrylate, trimethylolpropane triacrylate, pentaerythritol tetraacrylate, polyester polyol acrylates, polyetherol acrylates, and (meth)acrylates of singly to viginuply and more preferably triply to decuply ethoxylated, propoxylated or mixedly ethoxylated and propoxylated, and more particularly exclusively ethoxylated, neopentyl glycol, trimethylolpropane, trimethylolethane or pentaerythritol, e.g., triacrylate of singly to viginuply alkoxylated, more preferably ethoxylated, trimethylolpropane.

The radiation-curable coating composition may comprise the inventively prepared photoinitiator in an amount of, for example, 0.1% to 10% by weight, based on the total amount of compounds (A), (B), and (C). Additionally it is possible, based in each case on the sum of the compounds (A), (B), and (C), for there to be 0% to 10%, preferably 0.1% to 10%, by weight of at least one UV stabilizer (E), 0% to 5%, preferably 0.1% to 5%, by weight of suitable free-radical scavengers (F), and 0% to 10%, preferably 0.1% to 10%, by weight of further, typical coatings additives (G). Suitable stabilizers (E) comprise, for example, typical UV absorbers such as oxanilides, triazines, and benzotriazole (the latter available as Tinuvin® products from Ciba-Spezialitaten-chemie), and benzophenones. Examples of suitable free-radical scavengers (F) are sterically hindered amines such as 2,2,6,6-tetramethylpiperidine, 2,6-di-tert-butyl-piperidine or derivatives thereof, e.g., bis(2,2,6,6-tetramethyl-4-piperidyl) sebacate. Typical coatings additives (G) may be, for example, antioxidants, activators (accelerants), fillers, pigments, dyes, antistats, flame retardants, thickeners, thixotropic agents, surface-active agents, viscosity modifiers, plasticizers or chelating agents. Thickeners are, for example, free-radically (co)polymerized (co)polymers, customary organic and inorganic thickeners such as hydroxymethylcellulose or bentonite. Chelating agents may be, for example, ethylenediamineacetic acid and salts thereof and also β-diketones. Fillers comprise, for example, silicates, examples being silicates obtainable by hydrolysis of silicon tetrachloride, such as Aerosil® from Degussa, silaceous earth, talc, aluminum silicates, magnesium silicates, calcium carbonates, etc.

The coating materials of the invention are suitable for coating substrates such as wood, paper, textile, leather, nonwoven, plastics surfaces, glass, ceramic, mineral building materials, such as shaped cement bricks and fiber cement slabs, or coated or uncoated metals, preferably plastics or metals, more particularly in the form of films and foils, more preferably metals. The coating compositions may be used more particularly in primers, primer-surfacers, pigmented topcoat and clearcoat materials in the field of automotive refinish or large-vehicle finishing, and aircraft. More particularly the coating materials of the invention may be used as or in automotive clearcoat and topcoat material(s). Further preferred fields of use are cancoating and coilcoating.

EXAMPLES

Example 1

(Inventive): Polymerizable Photoinitiator

A reactor rendered partially inert with lean air (oxygen fraction 6%) is charged with 700 kg of 4-hydroxybenzophenone. While lean air is passed permanently through the reactor, 2250 kg of methyl ethyl ketone (MEK; fresh or recovered from an earlier batch) and 375 kg of triethylamine are pumped in. The batch is stabilized with 175 g of 2,2,6,6-tetramethylpiperidinyloxyl (TEMPO). Thereafter, at an internal temperature of 40° C., 737 kg of acryloyloxybutyl chloroformate are metered in and stirring is continued thereafter for 20 h. After that, 1030 kg of 5% strength hydrochloric acid are metered in. The lower, aqueous phase is separated off and the organic phase containing the product of value is stabilized with 150 g of TEMPO. To remove residual triethylamine and water fractions, a portion of the solvent present is removed by distillation. This is followed by stabilization with 2.5 kg of hydroquinone monomethyl ether solution in MEK, and by dilution with methyl ethyl ketone to the desired concentration. The contents of the reactor are cooled to −10° C. and discharged via a filter. This gives a solution of the polymerizable photoinitiator in methyl ethyl ketone with a content of 35% by weight and in a yield of approximately 93% (based on 4-hydroxybenzophenone).

Preparation of the Copolymers and of the Hotmelt PSA:

A copolymer solution is prepared by free-radical polymerization of the following constituents in methyl ethyl ketone:

Initial charge: 15.5 kg methyl ethyl ketone
Feed 1: 79.5 kg n-butyl acrylate
    4.2 kg acrylic acid
    0.6 kg photoinitiator of example 1 (in solution in methyl ethyl ketone, approximately 35% strength)
Feed 2: 0.1 kg free-radical initiator These constituents are polymerized at a temperature of 81° C., the components being fed in over the course of 4 hours. K value of the copolymer: 48-52.

Evaporation of the solvent produces a hotmelt PSA from the copolymer solution.

Example 2

(Noninventive, Prior Art)

A polymerizable photoinitiator, a copolymer solution, and a hotmelt PSA are produced as in example 1, with the difference that the photoinitiator is prepared in o-xylene rather than in methyl ethyl ketone, and the copolymer solution is prepared using a solution of the photoinitiator in o-xylene (approximately 35% strength).

Properties:

The properties of the hotmelt PSAs produced according to example 1 and example 2 are summarized in table 1.

TABLE 1

|  | Example 1 | Example 2 |
|---|---|---|
| VOC content | 160 ppm | 240 ppm |
| Volatile aromatic hydrocarbons content | 0 ppm | 70 ppm |
| Yellowness index[1] | 50 | 80 |

[1]Platinum cobalt color number (HAZEN color number) to DIN EN ISO 6271-1

Example 3

Cable-Wrapping Tape

A cable-wrapping tape of the invention may be produced for example as follows. Using a rolling rod nozzle, an inventive, UV-crosslinkable, acrylate hotmelt adhesive as per example 1 is applied at a rate of 50 m/min to a nonwoven carrier (Maliwatt, basis weight 80 g/m$^2$, linear density 22, from Cottano, for example). Coating may take place in different ways. In one variant, for example, adhesive may be applied at a temperature of 90 to 110° C. to the nonwoven at 80 g/m$^2$ in direct coating, with the bottom coating shaft being temperature-conditioned. In another version, 50 g/m$^2$ of adhesive can be coated onto a belt and transferred to the nonwoven carrier in a temperature conditionable laminating station at 80° C. under a pressure of 8 bar. This version permits particularly convenient control of the anchorage of the adhesive to the carrier material, with prevention of an unallowable strikethrough of adhesive. In the further belt course of the unit, the coated nonwoven carriers are crosslinked with UV lamps (e.g., with 6 medium-pressure Hg lamps each of 120 W/cm). The degree of crosslinking can be varied via the UV dose, allowing the technical properties (including bond strength and unwind force) to be set individually. The coated and irradiated nonwoven carriers may be wound up on cores on a core winder, to the desired lengths, and converted to the desired widths on an automatic slitting device. The adhesive tape is notable for a particularly low volatile organic compounds content, and more particularly by the absence of volatile aromatic hydrocarbons.

Example 4

Patch

A patch of the invention may be produced, for example, as follows. A patch film carrier of polyolefin having a specific mass per unit area of 56 g/m² has applied to it, using a rolling rod nozzle, at a speed of 80 m/min, a UV-crosslinkable acrylate hotmelt adhesive of the invention, as per example 1, in an amount of 38 g/m² and with a temperature of 145° C. Sufficient anchorage to the carrier may be achieved through thermal conditioning of the bottom coating shaft. The coated material is crosslinked by irradiation with ultraviolet light, as for example from four medium-pressure Hg lamps each of 120 W/cm. The degree of crosslinking can be varied by the UV dose, and so the corresponding technical properties (including bond strength and unwind force) may be set individually. The coated film is laminated with a siliconized paper, wound up to form a bale, and subjected to further processing to form adhesive tape rolls. The patch is notable for a particularly low volatile organic compounds content, more particularly for the absence of volatile aromatic hydrocarbons.

Example 5

Cable-Wrapping Tape which can be Wound onto Itself

The production of a cable-wrapping tape of the invention which can be wound onto itself may take place, for example, as follows. 80 g/m² of a UV-crosslinkable acrylate hotmelt adhesive of the invention, as per example 1, are applied to a polypropylene spunbonded nonwoven material having a basis weight of 40 g/m² and a thickness of 0.3 mm. Alternatively a polyester spunbonded nonwoven can also be used. After coating, the carrier can be wound up onto itself with a low tension. By applying an embossing pattern it is possible to achieve a further improvement in the noise-suppressing effect, for use of the adhesive tape for wrapping cable harnesses. The degree of crosslinking of the adhesive and the winding parameters for coating and converting may be chosen such that there is no blocking of the tape.

The adhesive tape is notable for a particularly low volatile organic compounds content, and especially for the absence of volatile aromatic hydrocarbons.

Example 6

General-Purpose Adhesive Tape which can be Wound onto Itself

The production of a general-purpose adhesive tape of the invention which can be wound onto itself may take place, for example, as follows. 90 g/m² of a UV-crosslinkable acrylate hotmelt adhesive of the invention, as per example 1, are applied to a polypropylene spunbonded nonwoven material having a basis weight of 50 g/m² and a thickness of 0.5 mm. Alternatively a polyester spunbonded nonwoven can also be used. After coating, the carrier is wound up onto itself with a low tension.

The adhesive tape is notable for a particularly low volatile organic compounds content, and especially for the absence of volatile aromatic hydrocarbons.

The invention claimed is:

1. A process for preparing a solution of at least one radiation-sensitive, free-radically polymerizable organic compound, comprising:
   i) esterifying
      a) a first starting compound, which has an acid halide group, and
      b) a second starting compound, which has an alcoholic hydroxyl group,
   in a solvent or solvent mixture and in the presence of a substantially stoichiometric amount of at least one tertiary organic amine to the amount of acid halide; wherein
   the solvent comprises one or more ketones having a boiling point of below 150° C. under atmospheric pressure (1 bar) or the solvent mixture is composed to an extent of at least 50% by weight, based on the amount of solvent, of said ketones; and
   one of the two starting compounds has at least one radiation-sensitive group and the other of the two starting compounds has at least one ethylenically unsaturated, free-radically polymerizable group; and
   ii) separating an organic ammonium halide which forms during the reaction by adding water in an amount such as to form a substantially saturated solution of said organic ammonium halide in water, and separating said saturated aqueous solution from an organic phase.

2. The process according to claim 1, wherein the first starting compound has a chloroformate group and an acrylate or methacrylate group and the second starting compound has an alcoholic hydroxyl group and a phenone group.

3. The process according to claim 1, wherein, after the saturated aqueous solution has been separated, residual fractions of ammonium salts that have remained in solution in the organic phase are precipitated by temperature reduction and separated.

4. The process according to claim 1, wherein at least part of said one or more ketones used are recycled hydrous ketones recovered from a prior preparation process.

5. The process according to claim 1, wherein an excess amine is removed by neutralization with acid and/or by distillation.

6. The process according to claim 1, wherein said one or more ketones are at least one ketone selected from the group consisting of acetone, methyl ethyl ketone and methyl isobutyl ketone.

* * * * *